United States Patent [19]

Cragoe, Jr.

[11] 4,394,385
[45] Jul. 19, 1983

[54] TREATMENT OF GRAY MATTER EDEMA

[75] Inventor: Edward J. Cragoe, Jr., Lansdale, Pa.

[73] Assignee: Merck & Co., Inc., Rahway, N.J.

[21] Appl. No.: 344,148

[22] Filed: Jan. 29, 1982

Related U.S. Application Data

[63] Continuation of Ser. No. 209,187, Nov. 21, 1980, abandoned, which is a continuation of Ser. No. 57,635, Jul. 16, 1979, abandoned, which is a continuation of Ser. No. 879,998, Feb. 22, 1978, abandoned.

[51] Int. Cl.³ ............................................. A61K 31/34
[52] U.S. Cl. .................................................... 424/285
[58] Field of Search ........................................ 424/285

[56] References Cited

U.S. PATENT DOCUMENTS 3,931,234 1/1976 Jernow et al. ...................... 424/275
3,984,552 10/1976 Cragoe et al. ...................... 424/250

FOREIGN PATENT DOCUMENTS 8436644 12/1976 Belgium .

OTHER PUBLICATIONS

Long et al., Dynamics of Brain Edema, pp. 293–300, Springer–Verlay (1976).

Primary Examiner—Stanley J. Friedman
Attorney, Agent, or Firm—William H. Nicholson; Edmunde D. Riedl; Mario A. Monaco

[57] ABSTRACT

The invention relates to the treatment of gray matter edema in the brain or spinal chord by the administration of benzofuranyloxyacetic acids, indeno[5,4-b]furancarboxylic acids, their analogs and salts thereof.

17 Claims, No Drawings

TREATMENT OF GRAY MATTER EDEMA

This is a continuation of application Ser. No. 209,187, filed Nov. 21, 1980 which is a continuation application of U.S. Ser. No. 57,635, filed July 16, 1979; which is a continuation application of U.S. Ser. No. 879,998, filed Feb. 22, 1978, all are now abandoned.

BACKGROUND OF THE INVENTION

Traumas to the brain caused by outside physical forces acting on the skull or spinal chord (hereinafter, head or spine injury), ischemic stroke, and hydrocephalus are all characterized by edema and resultant swelling. The standard treatment has been the administration of steroids, because of their known antiinflammatory activity or procedures such as the insertion of a shunt in the case of progressive hydrocephalus. Diuretics have not been used to treat brain and spinal chord edema partly because the blood-brain barrier prevents adequate concentrations of the diuretics from reaching brain cells. Thus, any decrease in edema following diuretic administration would be a secondary or independent effect resulting from general electrolyte loss and resultant dehydration of the rest of the body. Such dehydration would be inappropriate to someone with a traumatized brain or spinal chord.

Long, et al., *Dynamics of Brain Edema*, pp. 293-300, Springer-Verlag (1976) described the use of the diuretics furosemide and acetazolamide for the treatment of certain models of brain edema in cats.

Bourke, et al., *Brain Research*, 105 (1976) 309-323 described the effect of the diuretics ethacrynic acid and acetazolamide on swelling of monkey cerebrocortical slices.

SUMMARY OF THE INVENTION

The invention comprises the treatment of persons with gray matter edema. This edema can be the result of any of a variety of causes; for example, from external physical forces such as a blow to the head, neck or spine, a motor vehicle accident, or a fall, from ischemic stroke, from hydrocephalus, or from radiation. The treatment comprises administering to such a person an effective amount of a compound of the formulae:

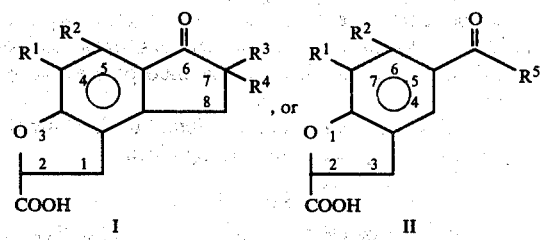

wherein
$R^1$ is H, $CH_3$ or Cl
$R^2$ is $CH_3$ or Cl
$R^3$ is alkyl or alkenyl of one through six carbons; cycloalkyl or cycloalkylalkyl of four through seven carbons; phenyl, unsubstituted or substituted with chloro or methyl; benzyl; or thienyl
$R^4$ is H, alkyl of one through five carbons, or $R^4$ and $R^3$ taken together with the carbon to which they are attached may be joined to form a cycloalkyl radical of five or six carbons, and $R^5$ is (1) furyl, (2) thienyl, (3) phenyl, unsubstituted or substituted with methyl, methoxy or halo, or (4) benzyl, unsubstituted or substituted with methyl or halo or the pharmaceutically acceptable salt, ester, or amide derivative thereof.

A further aspect of this invention is the concomitant administration of a compound of formula I or II with an antiinflammatory steroid for the treatment of gray matter edema of the brain or spinal chord.

DETAILED DESCRIPTION

The compounds of formulae I and II are known. Compounds of formula I are described in U.S. Pat. Nos. 3,984,552 (Oct. 5, 1976) and 3,931,239 (Jan. 6, 1976).

Compounds of formula II are described in Belgian Pat. No. 843,644 (Dec. 30, 1976).

By alkyl is meant both straight- and branched-chain alkyl such as methyl, ethyl, n-butyl, sec-butyl, iso-butyl, t-butyl pentyl and the like. Cycloalkyl includes cyclopropyl, cyclobutyl, cyclopentyl, and cyclohexyl. By halo is meant fluoro, chloro, and bromo.

Also included within the scope of this invention is the use of the enantiomeric forms of the compound of formulae I or II.

Preferred compounds of formulae I and II are those where $R^3$ is alkyl of one through five carbons, cycloalkyl or cycloalkylalkyl of five or six carbons, benzyl, phenyl, or together with $R^4$ is tetramethylene; $R^4$ is H or alkyl of one through five carbons; and $R^5$ is furyl, thienyl, benzyl, or phenyl substituted with chloro or methyl.

Other preferred compounds of formulae I and II are those where $R^1$ and $R^2$ are both chloro or both methyl, $R^3$ is alkyl of one through three carbons, phenyl, cyclopentyl, cyclohexyl or benzyl, $R^4$ is H, methyl or ethyl, $R^3$ together with $R^4$ are tetramethylene, and $R^5$ is furyl, thienyl, phenyl, p-chlorophenyl of p-methoxyphenyl.

A preferred compound is 4,5-dichloro-6-oxo-7-cyclopentyl-7-methyl-1,2,7,8-tetrahydro-6H-indeno[5,4,b]furan-2-carboxylic acid.

Another preferred compound is 4,5-dichloro-6-oxo-7-methyl-7-phenyl-1,2,7,8-tetrahydro-6H-indeno[5,4-b]furan-2-carboxylic acid (α-diastereomer).

Another preferred compound is 4,5-dichloro-6-oxo-7-methyl-7-phenyl-1,2,7,8-tetrahydro-6H-indeno[5,4-b]furan-2-carboxylic acid (β-diastereomer).

Another preferred compound of the invention is 4,5-dimethyl-6-oxo-7-propyl-1,2,7,8-tetrahydro-6H-indeno[5,4-b]furan-2-carboxylic acid.

Another preferred compound of the invention is 6,7-dichloro-5-(2-furoyl)-2,3-dihydrobenzofuran-2-carboxylic acid.

Another preferred compound of the invention is 6,7-dichloro-5-(2-thenoyl)-2,3-dihydrobenzofuran-2-carboxylic acid.

Another preferred compound of the invention is (+)6,7-dichloro-5-(2-thenoyl)-2,3-dihydrobenzofuran-2-carboxylic acid.

Another preferred compound of the invention is (−)6,7-dichloro-5-(2-thenoyl)-2,3-dihydrobenzofuran-2-carboxylic acid.

Included within the scope of this invention is the use of the salts, esters, and amide derivatives of formulae I or II compounds which are prepared by conventional methods well known to those skilled in the art. Thus, for example, the ester derivatives may be prepared by the reaction of the formulae I or II compounds of this invention with an alcohol, for example, with a lower alkanol.

The amide derivatives may be prepared by converting a formulae I or II compound to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amid compound. These and other equivalent methods for the preparation of the salts, esters, and amide derivatives of the instant products will be apparent to one having ordinary skill in the art and to the extent that said derivatives are both non-toxic and pharmacologically acceptable, said derivatives are the functional equivalent of the corresponding formulae I or II compounds. The preferred salts are: sodium, potassium, ammonium, ethanolamine, diethanolamine, triethanolamine, N-methylpiperazine, piperazine, cyclohexylamine, N-methylglucamine, N-methylglucosamine, tetramethylammonium, and the like.

Inasmuch as there is a wide variety of symptoms and severity associated with gray matter edema, particularly when it is caused by blows to the head or spinal chord, the precise treatment protocol is left to the practitioner. It is up to the practitioner to determine the patient's response to treatment and to vary the dosages accordingly. A recommended dosage range is from 1 μg to 2 mg/kg of body weight as a primary dose and a sustaining dose of half to equal the primary dose, every 12 to 24 hours.

The compounds of this invention can be administered by a variety of established methods, including intravenously, intramuscularly, subcutaneously, and orally. As with dosage, the precise mode of administration is left to the discretion of the practitioner.

Since some of the compounds used for this invention have diuretic properties which may vary in intensity from compound to compound, it is recommended that the person under therapy receive an intravenous infusion equivalent to the lost water and electrolyte. Here again the rate of infusion and the solutions used are left to the discretion of the practitioner.

Studies on human pathological tissues have revealed that ischemic insult to the brain is a major concomitant of head injury.

Recent studies in experimental head injury by R. S. Bourke et al. (R. S. Bourke, M. A. Daze' and H. K. Kimelberg, Monograph of the International Glial Cell Symposium, Leige, Belgium, Aug. 29-31, 1977 (in press) and references cited therein) and experimental stroke by J. H. Garcia et al. (J. H. Garcia, H. Kalimo, Y. Kamijyo and B. F. Trump, Virchous Archiv. B (1977), (in press) indicate that astroglial swelling, a secondary and potentially inhibitable process, is a fundamental pathophysiological response to ischemic/traumatic brain insult in both pathological disorders. Furthermore, astroglial swelling is believed to reduce oxygen available to neurons by prolongation of the oxygen diffusion pathway. Thus, the damage to cerebral grey matter may be far more extensive as a result of pathological events secondary to astroglial swelling than as a result of damage inflicted by the initial ischemic/traumatic insult. Consequently, it is of prime importance that the treatment commence as soon as possible after the initial trauma in order to minimize the brain cell damage and the possibility of death or permanent paralysis.

One aspect of this invention is the treatment of persons with gray matter edema by concomitant administration of compounds of formulae I or II or a pharmaceutically acceptable salt, ester, or amide thereof and of antiinflammatory steroids. These steroids are of some, albeit limited, use in control of white matter edema associated with ischemic stroke and head injury. Stereoid therapy is given according to established practice as a supplement to the compound of formula I or II, as taught elsewhere herein.

The compounds of formulae I or II are utilized by formulating them in a composition such as tablet, capsule or elixir for oral administration. Sterile solutions or suspensions can be used for parenteral administration. About 70 μg to 150 mg of a compound or mixture of compounds of formulae I or II, or a physiologically acceptable salt, ester, or amide is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are included to illustrate the preparation of representative dosage forms.

EXAMPLE 1

Dry-filled capsules containing 25 mg of active ingredient per capsule

|  | Per Capsule |
|---|---|
| 4,5-dichloro-6-oxo-7-cyclopentyl-7-methyl-1,2,7,8-tetrahydro-6H-indeno[5,4-b]furan-2-carboxylic acid | 25 mg |
| Lactose | 174 mg |
| Magnesium Stearate | 1 mg |
| Capsule (Size No. 1) | 200 mg |

The 4,5-dichloro-6-oxo-7-cyclopentyl-7-methyl-1,2,7,8-tetrahydro-6H-indeno[5,4-b]furan-2-carboxylic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsule can be prepared by replacing the active ingredient of the above example by any of the other compounds of this invention.

EXAMPLE 2

Parenteral Solution of Sodium 4,5-dichloro-6-oxo-7-cyclopentyl-7-methyl-1,2,7,8-tetrahydro-6H-indeno[5,4-b]furan-2-carboxylate 100 mg of sodium 4,5-dichloro-6-oxo-7-cyclopentyl-7-methyl-1,2,7,8-tetrahydro-6H-indeno[5,4-b]furan-2-carboxylate are dissolved in 3 ml. of 0.1 N-sodium hydrogen carbonate solution. The solution is made up to 10 ml with water and sterilized.

What is claimed is:

1. A method of treating persons with gray matter edema which comprises administering to such a person an effective amount of a compound of the formulae:

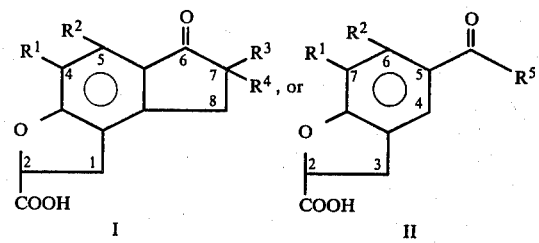

wherein
$R^1$ is H, $CH_3$ or Cl
$R^2$ is $CH_3$ or Cl
$R^3$ is alkyl or alkenyl of one through six carbons; cycloalkyl or cycloalkylalkyl of four through seven carbons; phenyl, unsubstituted or substituted with chloro or methyl; benzyl; or thienyl
$R^4$ is H, alkyl of one through five carbons, or $R^4$ and $R^3$ taken together with the carbon to which they are attached may be joined to form a cycloalkyl radical of five or six carbons, and $R^5$ is (1) furyl, (2) thienyl, (3) phenyl, unsubstituted or substituted with methyl, methoxy or halo, or (4) benzyl, unsubstituted or substituted with methyl or halo or the pharmaceutically acceptable salt, ester, or amide derivative thereof.

2. The method of claim 1 where $R^3$ is alkyl of one through five carbons, cycloalkyl or cycloalkylalkyl of four through six carbons, benzyl, phenyl or together with $R^4$ is tetramethylene; $R^4$ is H or alkyl of one through five carbons; and $R^5$ is furyl, thienyl, benzyl, or phenyl substituted with chloro or methyl.

3. The method of claim 2 where $R^1$ and $R^2$ are both chloro or both methyl; $R^3$ is alkyl of one through three carbons, phenyl cyclobutyl, cyclopentyl, cyclohexyl, or benzyl; $R^4$ is H, methyl, or ethyl; $R^3$ together with $R^4$ are tetramethylene; and $R^5$ is furyl, thienyl, benzyl, p-chlorophenyl, or p-methoxyphenyl.

4. The method of claim 3 where the compound is of formula I.

5. The method of claim 4 where $R^1$ and $R^2$ are chloro, and $R^3$ is phenyl, alkyl of one through three carbons, or cycloalkyl of four through six carbons.

6. The method of claim 5 where the compound is in α-diastereomer, $R^3$ is cyclopentyl and $R^4$ is methyl.

7. The method of claim 5 where the compound is in α-diastereomer, $R^3$ is phenyl and $R^4$ is methyl.

8. The method of claim 5 where the compound is the β-diastereomer, $R^3$ is phenyl and $R^4$ is methyl.

9. The method of claim 4 where $R^1$ and $R^2$ are methyl, $R^3$ is propyl, and $R^4$ is H.

10. The method of claim 3 where the compound is of formula II.

11. The method of claim 10 where $R^5$ is 2-furyl.

12. The method of claim 1 where the compound is in the + configuration.

13. The method of claim 1 where the compound is in the − configuration.

14. The method of claim 1 for treating persons with spinal chord injury.

15. The method of claim 1 for treating persons with hydrocephalus.

16. The method of claim 1 for treating persons with ischemic stroke.

17. The method of claim 1 for treating persons with head injury.

* * * * *